United States Patent [19]

Shattil

[11] Patent Number: 5,561,047
[45] Date of Patent: Oct. 1, 1996

[54] METHOD OF IDENTIFYING EFFECTORS OF INTEGRIN ACTIVATION

[75] Inventor: Sanford Shattil, Narberth, Pa.

[73] Assignee: The Trustees of the University of Pennsylvania, Philadelphia, Pa.

[21] Appl. No.: 354,943

[22] Filed: Dec. 13, 1994

[51] Int. Cl.$^6$ .................................................. G01N 33/567
[52] U.S. Cl. .................... 435/7.21; 435/7.24; 435/7.9; 435/13; 435/961; 436/503; 436/519; 436/548; 530/388.22; 530/388.7
[58] Field of Search ................................ 435/7.21, 7.24, 435/7.9, 13, 961; 436/503, 519, 548; 530/388.22, 388.7

[56] References Cited

U.S. PATENT DOCUMENTS

| | | | |
|---|---|---|---|
| 5,149,780 | 9/1992 | Plow et al. | 530/324 |
| 5,169,836 | 12/1992 | Shattil et al. | 514/13 |
| 5,196,309 | 3/1993 | Ginsberg | 435/7.21 |
| 5,262,520 | 11/1993 | Plow et al. | 530/326 |
| 5,306,620 | 4/1994 | Ginsburg et al. | 435/7.2 |

OTHER PUBLICATIONS

S. Shattil et al, "Regulation of Fibrinogen Receptor Expression on Human Platelets," Abstract #1116 in *Federation of American Societies for Exper. Biology*, 45(3):346, 1986.

Abrams, C. S. et al., "Anti–idiotypic Antibodies against an Antibody to the Platelet Glycoprotein (GP) IIb–IIIa Complex Mimic GP IIb–IIIa by Recognizing Fibrinogen", *J. Biol. Chem.* 1992, 267, 2775–2785.

Abrams, C. S. et al., "Direct Detection of Activated Platelets and Platelet–Derived Microparticles in Humans", *Blood* 1990, 75, 128–138.

Alig, L. et al., "Low Molecular Weight, Non–Peptide Fibrinogen Receptor Antagonists", *J. Med. Chem.* 1992, 35, 4393–4407.

Bennett, J. S. et al., "Inhibition of Fibrinogen Binding to Stimulated Human Platelets by a Monoclonal Antibody", *Proc. Natl. Acad. Sci. USA* 1983, 80, 2417–2421.

Bennett, J. S. and Vilaire, G., "Exposure of Platelet Fibrinogen Receptors by ADP and Epinephrine", *J. Clin. Invest.* 1979, 64, 1393–1401.

Coller, B. S., "Antiplatelet Agents in the Prevention and Therapy of Thrombosis", *Annu. Rev. Med.* 1992, 43, 171–180.

Coller, B. S., "A New Murine Monoclonal Antibody Reports an Activation–dependent Change in the Conformation and/or Microenvironment of the Platelet Glycoprotein IIb/IIIa Complex", *J. Clin. Invest.* 1985, 76, 101–107.

Diamond, M. S. et al., "The Dynamic Regulation of Integrin Adhesiveness," *Curr. Biol.* 1994, 4, 506–517.

The Epic Investigators, "Use of a Monoclonal Antibody Directed Against the Platelet Glycoprotein IIb/IIIa Receptor in High–Rosk Coronary Angioplasty," *New Engl. J. Med.* 1994, 330, 956–961.

Ginsberg, M. H. et al., "Inside–out Integrin Signalling", *Curr. Opin. Cell Biol.* 1992, 4, 766–771.

Graber, S. E. and Hawiger, J., "Evidence That Changes in Platelet Cyclic AMP Levels Regulate the Fibrinogen Receptor on Human Platelets", *J. Biol. Chem.* 1982, 257, 14606–14609.

Hynes, R. O., "Integrins: Versatility, Modulation, and Signaling in Cell Adhesion", *Cell* 1992, 69, 11–25.

Michelson, A. D., "Platelet Activation by Thrombin Can Be Directly Measured in Whole Blood through the Use of the Peptide GPRP and Flow Cytometry: Methods and Clinical Applications," *Blood Coagul. Fibrinolysis* 1994, 5, 121–131.

Nguyen, B. L., et al., "Interaction of Nitric Oxide and cGMP with Signal Transduction Activated Platelets," *Am. J. Physiol. Heart Circ. Physiol.* 1991, 261, H1043–H1052.

O'Toole, T. E. et al., "Integrin Cytoplasmic Domains Mediate Inside–Out Signal Transduction," *J. Cell. Biol.* 1994, 124, 1047–1059.

Picker, L. J. et al., "Coordinate expression of $\beta 1$ and $\beta 2$ integrin activation epitopes during T cell responses in secondary lymphoid tissue", *Eur. J. Immunol.* 1993, 23, 2751–2757.

Plow, E. F. et al., "The effect of Arg–Gly–Asp–containing peptides on fibrinogen and von Willebrand factor binding to platelets", *Proc. Natl. Acad. Sci. USA* 1985, 82, 8057–8061.

Shattil et al., "Detection of Activated Platelets in Whole Blood Using Activation–Dependent Monoclonal Antibodies and Flow Cytometry", *Blood* 1987, 70, 307–315.

Shattil, S. J. et al., "Changes in the Platelet Membrane Glycoprotein IIb–IIIa Complex during Platelet Activation", *J. Biol. Chem.* 1985, 260, 11107–11114.

Shattil, S. J. et al., "Adhesive signaling in platelets", *Curr. Opin. Cell Biol.* 1994, 6, 695–704.

Siess, W., "Molecular Mechanisms of Platelet Activation," *Physiol. Rev.* 1989, 69, 58–178.

Smyth, S. et al., "Regulation of Ligand Binding to Glycoprotein IIb–IIa (integrin $\alpha_{IIb}\beta_3$) in Isolated Platelet Membranes," *Biochem. J.* 1993, 292, 749–758.

Toullec, D. et al., "The Bisindolylmaleimide GE 109203X Is a Potent and Selective Inhibitor of Protein Kinase C", *J. Biol. Chem.* 1991, 266, 15771–15781.

van Kooyk, Y. et al., "Activation of LFA–1 through a $Ca^{2+}$–dependent Epitope Stinulates Lymphocyte Adhesion", *J. Cell Biol.* 1991, 112, 345–354.

Woods, V. L. et al., "Resting Platelets Contain a Substantial Centrally Located Pool of Glycoprotein IIb–IIIa Complex Which May be Accessible to Some but Not Other Extracellular Proteins", *J. Biol. Chem.* 1986, 261, 15242–15242.

*Primary Examiner*—Carol A. Spiegel
*Attorney, Agent, or Firm*—Law Offices of Jane Massey Licata

[57] ABSTRACT

A method of identifying compounds that effect integrin activation in intact cells is provided.

4 Claims, No Drawings

1

METHOD OF IDENTIFYING EFFECTORS OF INTEGRIN ACTIVATION

INTRODUCTION

This invention was made in the course of research sponsored by the National Institutes of Health. The U.S. Government may have certain rights in this invention.

BACKGROUND OF THE INVENTION

Integrins are heterodimeric cell surface adhesion receptors, each composed of an α and β type I transmembrane subunit (Hynes, R. O., *Cell* 1992, 69, 11). Integrin $\alpha_{IIb}\beta_3$ is platelet-specific and plays a key role in hemostasis and thrombosis by binding to arginine-glycine-aspartic acid (RGD)-containing adhesive ligands (e.g., fibrinogen, von Willebrand factor) (Shattil, S. J. et al., *Curr. Opin. Cell Biol.* 1994, 6, 695–704). A notable feature of this ligand-receptor interaction is its regulation by the cell. Platelets normally circulate in a "resting" state in which the apparent affinity of $\alpha_{IIb}\beta_3$ for ligands is low. However, the addition of a physiological agonist, such as thrombin or ADP, or of a direct activator of protein kinase C, such as phorbol myristate acetate (PMA), causes a rapid increase in receptor affinity, resulting in ligand binding and platelet aggregation (Bennett, J. S. and Vilaire, G., *J. Clin. Invest.* 1979, 64, 1393). This increase in affinity can be prevented or reversed by compounds that stimulate an increase in intracellular cyclic AMP, such as prostaglandin $I_2$ ($PGI_2$); or in cyclic GMP, such as nitric oxide (Grager, S. E. and Hawiger, J., *J. Biol. Chem.* 1982, 257, 14606; Nguyen, B. L. et al., *Am. J. Physiol. Heart Circ. Physiol.* 1991, 261, H1043). It is believed that the intracellular signals generated by agonists (or antagonists) trigger modifications in the cytoplasmic domains of the integrin subunits, thus leading to conformational changes in the extracellular portion of the receptor that increase (or decrease) accessibility of the ligand-binding site (Ginsberg, M. H. et al., *Curt. Opin. Cell Biol.* 1992, 4, 766).

SUMMARY OF THE INVENTION

The present invention provides a method of identifying effectors of integrin activation in intact cells, preferably platelets, which comprises contacting intact cells suspended in assay medium with a test compound and a known integrin activator, incubating these cells with an integrin binding agent under conditions so that the integrin binding agent can bind to any activated integrin on the cells, separating the cells from the assay medium, determining the amount of unbound integrin binding agent in the assay medium, and comparing the amount determined with established controls. By using intact, activated cells, the method of the present invention allows for screening of potential integrin effectors, meaning either inhibitors or agonists, that specifically inhibit or activate integrin activation without necessarily affecting other cellular responses, such as secretion.

DETAILED DESCRIPTION OF THE INVENTION

Compounds that specifically block integrin activation without affecting other platelet responses have not yet been identified. A primary reason for this is that the screening process for such compounds is more complicated than that for related effectors such as inhibitors of ligand binding. For example, identification of inhibitors of ligand binding has been facilitated by the finding that the RGD sequence is an integrin-recognition motif common to most $\alpha_{IIb}\beta_3$ ligands (Plow, E.F. et al., *Proc. Natl. Acad. Sci. USA* 1985, 82, 8057). In contrast, the structural requirements for specific inhibition of activation of the major platelet integrin, $\alpha_{IIb}\beta_3$, are unknown. Furthermore, studies of ligand binding to $\alpha_{IIb}\beta_3$ have been facilitated by the use of paraformaldehyde-fixed platelets and even activated forms of purified or recombinant $\alpha_{IIb}\beta_3$ (Shattil, J. S. et al., *Blood* 1987, 70, 307; Alig, L. et al., *J. Med. Chem.* 1992, 35, 4393; O'Toole, T. E. et al., *J. Cell. Biol.* 1994, 124, 1047). However, these forms of the receptor cannot be used to identify intracellular inhibitors of integrin activation because dynamic regulation of integrins such as $\alpha_{IIb}\beta_3$ by agonists has been observed only in the intact, metabolically active platelets (Smyth, S. S. and Parise, L. V. *Biochem. J.* 1993, 292, 749). The method of the present invention overcomes these problems by using intact, active cells to identify potential integrin effectors. By "effectors" it is meant to include both inhibitors and agonists of integrin activation.

Compounds that inhibit activation of integrins such as $\alpha_{IIb}\beta_3$ are believed to be therapeutically useful in clinical situations associated with occlusive platelet thrombi, such as unstable angina, acute myocardial infarction, abrupt vascular occlusion after coronary angioplasty, or transient ischemic attacks. Related compounds, antibody, peptidic and non-peptidic inhibitors of fibrinogen binding to $\alpha_{IIb}\beta_3$ are currently undergoing clinical trials (The Epic Investigators, *New Engl. J. Med.* 1994, 330, 956). The effectiveness of these compounds as platelet aggregation inhibitors appears to be directly related to their ability to occupy $\alpha_{IIb}\beta_3$ and block ligand binding (Coller, B. S., *Annu. Rev. Med.* 1992, 43, 171).

Compounds that activate platelet integrin and ligand binding, also referred to as agonists may be used in clinical situations associated with impaired blood coagulation such as in liver and kidney diseases which cause a reduction in platelet function. The administration of a platelet integrin $\alpha_{IIb}\beta_3$ activator in such situations would improve blood clotting under conditions of reduced platelet function.

In the present invention a method is provided for identifying effectors of integrin activation in intact platelets. While much of this disclosure is focused on the major platelet integrin, $\alpha_{IIb}\beta_3$, one of skill in the art upon this disclosure could routinely adapt the method of the present invention to integrins of other cells. For example, $\beta_1$ and $\beta_2$ integrins on leukocytes and endothelial cells play important roles in immune and inflammatory responses and, in these settings, affinity modulation is a major mechanism of integrin regulation (Diamond, M.S. and Springer, D.A., *Curr. Biol.* 1994, 4, 506; Hynes, R.O., *Cell* 1992, 69, 11). Accordingly, the method of the present invention is not limited to platelet integrins but rather is useful in identifying and characterizing pharmacological inhibitors and activators of integrins in cells other than platelets and in clinical situations other than hemostasis and thrombosis.

This method comprises contacting a sample of intact cells, preferably platelets, suspended in assay medium with a test compound and a known integrin activator. Intact platelets used in the present invention are isolated from the blood of any mammal. The use of fresh platelets is an advantage of the method because they allow for the screening of integrin effectors under conditions of dynamic integrin function in active, intact platelets. The number of platelets obtained from 1 unit of blood is sufficient for 2500 test wells. The number of platelets used in a sample must be of sufficient concentration to provide enough integrin receptors for discrimination between unactivated and activated platelets. Such concentration can be easily determined in accordance with the teachings of the present invention through the use of known integrin activators. Examples of known platelet integrin activators which are used in the present invention include, but are not limited to, platelet myristate acetate (PMA), thrombin, and ADP. Such activators are used in the present invention in the presence of a test compound to measure the ability of the test compound to inhibit activation of the platelets.

The intact cells are then incubated with an integrin binding agent under conditions in which the agent will bind to any activated integrin of the intact cells. By "integrin binding agent" it is meant an agent capable of binding selectively to the extracellular portion of an activated integrin, for example, an antibody. In a preferred embodiment wherein the intact cells are platelets, the integrin binding agent is referred to as a fibrinogen mimetic. By "fibrinogen mimetic", it is meant an agent capable of binding selectively to an activated form of a platelet integrin such as $\alpha_{IIb}\beta_3$. An example of a fibrinogen mimetic which is used in the present invention is an antibody which binds specifically to activated integrin $\alpha_{IIb}\beta_3$ such as PAC1 (U.S. Pat. No. 5,169,836). Antibodies specific to other integrins can also be used in the present invention. For example, monoclonal antibodies specific for activated forms of certain $\beta_1$ and $\beta_2$ integrins have recently been developed (van Kooyk, Y. et al., *J. Cell Biol.* 1991, 112, 345; Picker, L.J. et al., *Eur. J. Immunol.* 1993, 23, 2751; Diamond, M.S. and Springer, D.A., *Curr. Biol.* 1994, 4, 506). These antibodies may be used in the present invention to detect activation of integrins in intact cells other than platelets such as leukocytes and endothelial cells.

The intact cells are then separated from the assay medium and the amount of unbound integrin binding agent in the substantially cell-free assay medium is determined. Cells can be separated from the assay medium by any number of different methods routine to those of skill in the art. By "substantially cell-free assay medium" it is meant an assay medium containing less than approximately $1\times10^4$ cells; preferably, less than $1\times10^4$ cells; more preferably, less than $1\times10^2$ cells in the aliquot used for analysis of unbound integrin binding agent. Centrifugation is a preferred method of separation. The amount of any unbound integrin binding agent such as a fibrinogen mimetic in the substantially cellfree assay medium is determined by a number of different means. For example, in one embodiment, the detection involves the detection of unlabelled fibrinogen mimetic by a specific antibody. In another embodiment, the fibrinogen mimetic is labelled and the label is detected. The label can be covalently attached to the fibrinogen mimetic and can include, but is not limited to, biotin, a radiolabel, a fluorophore, a secondary antibody, or other uniquely recognizable molecular moiety.

In a preferred embodiment of the invention, the detection of the fibrinogen mimetic is by enzyme-linked immunosorbent assay (ELISA). A streptavidin-coated support material such as a microtitre well is used to capture any unbound biotin-labeled fibrinogen mimetic in the substantially cell-free assay medium. In a preferred embodiment of the invention using the ELISA format, a biotinylated IgM murine monoclonal antibody, PAC1, is employed as the fibrinogen mimetic. Streptavidin binds the biotinylated PAC1 in the substantially cell-free assay medium. Once the platelet supernatants have been obtained and the streptavidin-coated plates have been prepared, both can be stored at −70° C. for at least several months, if necessary, before the assay is completed. Goat anti-mouse IgM-horseradish peroxidase conjugate activates a substrate such as o-phenylenediamine dihydrochloride and the product of the peroxidase reaction is monitored at 490 nm.

The amount of unbound fibrinogen mimetic determined in the assay medium is then compared to established controls. Known integrin activators serve as established controls for comparison of the activity of a test compound. In addition known integrin inhibitors also serve as established controls. Examples of known integrin inhibitors include, but are not limited to, compounds that stimulate an increase in intracellular cyclic AMP levels (e.g., prostaglandin I2 ($PGI_2$)); or compounds that stimulate an increase in cyclic GMP such as nitric oxide. It is preferred that $PGI_2$ be used as an established inhibitor control. In a preferred embodiment of the invention, separate established controls containing either a known integrin activator or a known integrin inhibitor are run in platelet samples simultaneously for comparison with the test compound. An established control containing intact platelets suspended in assay medium and a known integrin activator and an established control containing intact platelets suspended in assay medium and a known integrin inhibitor are prepared. These controls are treated in the same manner as the sample containing the test compound. They are contacted with the same condentration of fibrinogen mimetic as the platelet sample containing the test compound and incubated under the same conditions. Following incubation, amounts of unbound fibrinogen mimetic are determined in the separated assay medium from each of the controls. The determined amounts from each of the established controls are then compared to the determined amount in the platelet sample containing the test compound to determine whether the test compound affected integrin activation. Test compounds which are platelet integrin inhibitors have determined amounts of unbound fibrinogen mimetic similar to the amount determined in the established control containing the known integrin inhibitor. Test compounds which are platelet integrin agonist or activators have determined amounts of unbound fibrinogen mimetic similar to the amount determined in the established control containing the known integrin activator.

By "platelet integrin inhibitor" is meant a chemical compound, peptide, or protein that inhibits binding of a ligand to the extracellular portion of the integrin heterodimer in intact, active platelets under the conditions of the method of the invention. An inhibitor can act extracellularly by blocking binding to the extracellular portion. An inhibitor can also act intracellularly by interacting with the intracellular portion of the platelet integrin heterodimer to cause conformational changes within the heterodimer to inhibit ligand binding to the extracellular portion. Inhibitors which function intracellularly are presented to the cells such that the cells are capable of incorporating the inhibitor into the intracellular domain by methods well known to those of ordinary skill in the art of pharmacology and drug delivery.

By "platelet integrin activator" or "platelet integrin agonist" is meant a chemical compound, a peptide, or protein that activates binding of a ligand to the integrin heterodimer in intact, active platelets under the conditions of the method of the invention. Am agonist can act extracellularly or intracellularly by inducing a change in either the conformation and/or microenvironment of integrin such that ligands can interact with a portion of the complex possessing a high binding affinity.

In addition to being a useful method for identifying compounds as potential selective, effectors of integrin activation, the method of the present invention is also useful in determining the degree of $\alpha_{IIb}\beta_3$ blockade after in vivo administration of antagonists of ligand binding. The most relevant compartment for such inhibitors appears to be the platelet surface and not the plasma. For example, after infusion of antibody 7E3 Fab into patients, more than 90% of platelet $\alpha_{IIb}\beta_3$ had to be occupied and blocked by the antibody in order for significant inhibition of ex-vivo platelet aggregation to be observed (Coller, B.S. et al., *Annals NY Acad. Sci.*1991, 614, 193). Thus, by using slight modifications of the assay described here, it should be possible to measure the degree of occupancy of $\alpha_{IIb}\beta_3$ by a tightly-bound drug from the direct analysis of platelets in whole blood. The presence of plasma and other blood cells in a sample does not interfere with the measurement of PAC1 binding to platelets (Shattil et al., *Blood* 1987, 70, 307; Abrams, C.S. et al., *Blood* 1990, 75, 128).

The following nonlimiting examples are provided for illustrative purposes.

EXAMPLES

Example 1

Materials

Murine monoclonal antibodies $A_2A_9$ (IgG$_{2a}$) and 7E3 (Fab) recognize $\alpha_{IIb}\beta_3$ on resting and activated platelets (Bennett, J.S. et al., *Proc. Natl. Acad. Sci. USA* 1983, 80, 2417; Coller, B.S., *J. Clin. Invest.* 1985, 76, 101); $B_1B_5$ (IgG$_1$) is specific for $\alpha_{IIb}$ and SSA6 (IgG$_1$) for $\beta_3$ (Abrams, C.S. et al., *J. Biol. Chem.* 1992, 267, 2775). Monoclonal antibodies were purified using established methods (Shattil, S. J. at al., *J. Biol. Chem.* 1985, 260, 11107; Abrams, C. S. et al., *J. Biol. Chem.* 1992, 267, 2775) PAC1 (IgM) was biotinylated in accordance with known methods (Shattil et al., *Blood* 1987, 70, 307). Ro43-5054 is an anti-$\alpha_{IIb}\beta_3$ peptidomimetic (Alig, L. et al., *J. Med. Chem.* 1992, 35, 4393). Affinity-purified goat anti-mouse IgM-horseradish peroxidase conjugate (1:1500) was from GIBCO BRL Life Technologies, Inc., Grand Island, N.Y. Affinity-purified streptavidin was from PIERCE, Rockford, Ill. Thrombin and bisindolylmaleimide were obtained from Calbiochem-Novabiochem Corporation, La Jolla, Calif. All other reagents and chemicals were obtained from Sigma Chemical Company, St. Louis, Mo.

Platelet incubations were carried out in wells of Falcon flexible polyvinyl chloride (PVC) microtitre plates with 96 U-bottom wells (Becton Dickinson, San Jose, Calif.). ELISA reactions were carried out in 96 well Immulon II polystyrene plates (Dynatech Laboratories, Inc., Chantilly, Va.) that had been precoated with streptavidin. This was accomplished by addition of 75 µl/well of streptavidin (1.25 µg/ml) for 16 hours at 4°, followed by washing four times with 200 µl of 1% TWEEN(polyethylenesorbit −20 in phosphate-buffered saline (PBS), pH 7.4, blocking with 200 µl of 1% bovine serum albumin in PBS for 2 hours at room temperature, and washing again. These plates could be stored at −20° for at least 3 months prior to use in the assay.

Example 2

Preparation of washed platelets

Whole blood was obtained from healthy, drug-free volunteers and anticoagulated with a 1:6 volume of acid-citrate-dextrose formula A. Platelet-rich plasma was collected by centrifugation at 180×g for 20 minutes, incubated for 5 minutes with 1 µM prostaglandin E$_1$ and 1 unit/ml apyrase, then sedimented at 500×g for 10 minutes and resuspended in 5 ml of 2 wash buffer containing 20 mM HEPES, 0.15 M NaCl, 0.1% glucose, 1 µM prostaglandin E$_1$, 1 unit/ml apyrase, and 1.5 mM EDTA, pH 7.4. After another centrifugation at 500×g for 20 minutes, the platelets were finally resuspended to $5.8\times10^8$/ml in an incubation buffer containing 137 mM NaCl, 2.7 mM KCl, 1.0 mM MgCl$_2$, 3.3 mM NaH$_2$PO$_4$, 0.1% glucose, 0.1% bovine serum albumin, and 20 mM HEPES, pH 7.35.

Example 3

Incubation of resting and activated platelets with biotin-PAC1

Fifty-five µl of washed platelets were added in triplicate to wells of PVC plates containing 10 µl of the desired agonist (or the activation inhibitor, PGI$_2$) and 25 µl of the desired inhibitory test compound (or the equivalent vehicle as a diluent). After 10 minutes at 37° without shaking, 10 µl of biotin-PAC1 were added to achieve a final antibody concentration of 0.5 µg/ml and a platelet concentration of $3.2\times10^8$/ml. After a further 15 minutes incubation at room temperature without shaking, the microtitre plates were centrifuged at 2800 rpm for 10 minutes to sediment the platelets, conditions under which essentially all of the platelets were removed from the supernatant.

Example 4

Quantitation of unbound biotin-PAC1 by ELISA

After platelet centrifugation, 50 µl of supernatant from each well were transferred to corresponding wells of streptavidin-coated plates and incubated for 30 minutes at room temperature. Each well was then washed four times with 200 µl of PBS/Tween, followed by addition of 50 µl of goat anti-mouse IgM-horseradish peroxidase conjugate (1:1500). After incubation for 60 minutes at room temperature, the plates were again washed four times with PBS/Tween, followed by addition of 50 µl of a reaction mixture containing 1 mg/ml o-phenylenediamine dihydrochloride and 0.012% H$_2$O$_2$ in 0.1 M citrate buffer, pH 4.5. After a final 20 minutes at room temperature, reactions were stopped with 25 µl of 4 N HCl, and formation of the reaction product was measured at 490 nm in a THERMOmax microplate reader (Molecular Devices, Inc.)

Example 5

Screening of platelet integrin $\alpha_{IIb}\beta_3$ effectors by ELISA

Triplicate aliquots of washed human platelets were incubated in microtitre wells at a final volume of 90 µl in the presence of a platelet agohist such as PMA or thrombin, in order to convert $\alpha_{IIb}\beta_3$ into a high affinity, ligand-competent state. Compounds that were being tested for their ability to inhibit $\alpha_{IIb}\beta_3$ were also added to some of the wells at this stage. Other wells contain PGI$_2$ (0.2 µM), a potent platelet activation inhibitor, to purposely maintain $\alpha_{IIb}\beta_3$ in a low-affinity state. After 10 minutes at 37°, 10 µl of a subsaturating and limiting concentration of biotin-PAC1 was added to each well and the incubation was continued for an additional 15 minutes at room temperature.

The microtitre plates were then centrifuged at 2800 rpm for 10 minutes in order to sediment the platelets. Platelets in wells that contain PGI$_2$ do not have bound biotin-PAC1 and the antibody is retained in the supernatant. In contrast, platelets in wells containing an agonist have bound biotin-PAC1. Thus, some of the biotin-PAC1 is sedimented with the platelets during this centrifugation step, leaving the supernatant depleted of the antibody. Thus, if a test compound inhibits agonist-induced $\alpha_{IIb}\beta_3$ activation and biotin-PAC1 binding, there is less depletion of PAC1 from the supernatant.

The amount of biotin-PAC1 remaining in the supernatant was determined by transferring 50 μl aliquots to streptavidin-coated microtitre wells. Biotin-PAC1 was allowed to bind to the streptavidin for 30 minutes at room temperature, followed by washing. The bound biotin-PAC1 was quantitated by ELISA using goat anti-mouse IgM antibody conjugated to horseradish peroxidase as the enzyme source, o-phenylenediamine dihydrochloride as the substrate. The reaction product was monitored at 490 nm. The amount of biotin-PAC1 bound to platelets was determined by subtracting the amount of biotinPAC1 remaining in the supernatant of $PGI_2$-treated platelets from the amount remaining in the supernatant of agonist-activated platelets. This difference was expressed in optical density units as "$\Delta OD_{490}$ nm" and it is referred to hereafter as "platelet-bound biotin-PAC1".

Example 6

Optimization of assay conditions

Assay variables in each step of the assay were examined systematically. First, it was shown that $\alpha_{IIb}\beta_3$ did not become artifactually activated during preparation of washed platelets. Flow cytometry was used to assess the activation state of the platelets using FITC-PAC1 as the activation marker (Shattil et al., *Blood* 1987, 70, 307). No activation of washed platelets was detected. In a representative experiment, mean FITC-PAC1 binding to washed platelets was 22 arbitrary fluorescence units, a value identical to that obtained with platelets in whole blood or in platelet-rich plasma. FITC-PAC1 binding to washed platelets that had been stimulated for 15 minutes with 0.2 mM phorbol myristate acetate amounted to 1,776 fluorescence units.

The optimal coating concentration of streptavidin for the plates was selected. The amount of biotin-PAC-1 bound to streptavidin-coated wells was dependent on the input concentrations of both biotin-PAC1 and streptavidin. At any given biotin-PAC1 concentration, there was a progressive increase in PAC1 bound at streptavidin coating concentrations between 0.15–2.5 μg/ml. For example, at a streptavidin coating concentration of 1.25 μg/ml, biotin-PAC1 binding increased progressively at PAC1 concentrations between 0.1–1.5 μg/ml and then leveled off at higher antibody concentrations. Accordingly, in subsequent studies, the streptavidin coating concentration was fixed at 1.25 μg/ml and the biotin-PAC1 concentration at 0.5 μg/ml.

The optimal input concentration of platelets to be used was selected. It was also shown that biotin-PAC1 was limiting under the conditions of the assay. When platelets were activated with the potent agonist, PMA (0.2 μM), in the presence of 0.5 μg/ml biotin-PAC1, the amount of biotin-PAC1 remaining in the supernatant after centrifugation of the platelets decreased as the number of activated platelets in the well increased. No depletion of PAC1 was observed at any platelet concentration in wells containing $PGI_2$-treated, unactivated platelets. Therefore, in subsequent experiments, $0.32 \times 10^8$ platelets were added to each well, thus providing a sufficient number of $\alpha_{IIb}\beta_3$ receptors for good assay discrimination between unactivated and activated platelets.

Example 7

Detection of $\alpha_{IIb}\beta_3$ activation in response to physiological platelet agonists PMA at 0.2 μM activates protein kinase C and causes maximal activation of $\alpha_{IIb}\beta_3$ in conventional radioligand binding and flow cytometric assays (Shattil et al., *Blood* 1987, 70, 307). This concentration of PMA also caused maximal activation of $\alpha_{IIb}\beta_3$ as detected in the integrin activation ELISA. The physiological agonists, ADP and thrombin, also caused $\alpha_{IIb}\beta_3$ activation in a dose-dependent manner. ADP-induced activation was half-maximal at about 1 μM and maximal at 10 μM, while thrombin was half-maximal at 0.015 U/ml and maximal at 0.1 U/ml. The extent of biotin-PAC1 binding observed with maximal concentrations of thrombin and PMA was similar, while binding with ADP was less. It appears that in unstirred platelets, thrombin and PMA, but not ADP, stimulate the surface expression of an "internal" pool of activated $\alpha_{IIb}\beta_3$ (Woods, V. L. et al., *J. Biol. Chem.* 1986, 261, 15242).

Example 8

Detection of blockade of $\alpha_{IIb}\beta_3$ by known inhibitors of fibrinogen binding Since PAC1 is a fibrinogen mimetic, the assay of the present invention is capable of detecting inhibition of PAC1 binding to platelets by fibrinogen or known inhibitors of fibrinogen binding. Biotin-PAC1 binding to activated platelets was inhibited by fibrinogen with an $IC_{50}$ of 400 nM and by unlabeled PAC1 with an $IC_{50}$ of 20 nM. Furthermore, biotin-PAC1 binding was inhibited in a dose-dependent manner by the RGD peptide, RGDS, and by the $\alpha_{IIb}\beta_3$-selective peptidomimetic, Ro 43–5054. In contrast, RGES, which does not inhibit fibrinogen binding, was ineffective. Biotin-PAC1 binding was also blocked by anti-$\alpha_{IIb}\beta_3$ monoclonal antibodies that inhibit fibrinogen binding (A2A9, 7E3), but not by anti-$\alpha_{IIb}\beta_3$ antibodies that do not inhibit fibrinogen binding (B1B5; SSA6). These direct inhibitors of ligand binding were still effective when platelets had first been activated by PMA and then fixed with paraformaldehyde prior to testing. This is consistent with previous observations that activated $\alpha_{IIb}\beta_3$ can bind ligands after platelet fixation with paraformaldehyde (Shattil et al., *Blood* 1987, 70, 307; Michelson, A. D., *Blood Coagul. Fibrinolysis* 1994, 5, 121). Modulation of receptor affinity by agonists or intracellular antagonists will not take place in fixed platelets (Shattil et al., *Blood* 1987, 70, 307). Thus, once a test compound is identified as an $\alpha_{IIb}\beta_3$ inhibitor, fixed platelets can be used to determine whether the compound primarily blocks integrin activation or ligand binding.

Example 9

Detection of inhibitors of $\alpha_{IIb}\beta_3$ activation

Most available intracellular inhibitors of platelet activation affect multiple platelet responses and, therefore, are not specific for $\alpha_{IIb}\beta_3$ activation. However, some of these compounds were tested to determine whether this assay could detect intracellular inhibition of integrin activation. Bisindolylmaleimide is a selective inhibitor of protein kinase C in platelets and is maximally effective at 10–20 μM (Toullec, D. et al., *J. Biol. Chem.* 1991, 266, 15771). In the method of the present invention, bisindolylmaleimide inhibited biotin-PAC1 binding to PMA-stimulated platelets with an $IC_{50}$ of approximately 1 μM and inhibition was complete at 20 μM. 2-Deoxyglucose and antimycin A inhibit glucose metabolism and ATP production and block both platelet aggregation and secretion (Sless, W., *Physiol. Rev.* 1989, 69, 58). A combination of these two compounds inhibited biotin-PAC1 binding to PMA-activated platelets in a dose-dependent manner. Similar results were obtained with thrombin-stimulated platelets. Thus, this assay is sensitive to inhibitors of $\alpha_{IIb}\beta_3$ activation whose locus of action is inside the platelet.

What is claimed:

1. A method of identifying an inhibitor of integrin activation in intact platelets comprising:

a) contacting the intact platelets suspended in culture medium with a test compound and a known integrin activator to form a reaction mixture, said intact platelets having integrin which can become activated;

b) incubating the intact platelets with a fibrinogen mimetic added to the reaction mixture under conditions so that the fibrinogen mimetic can specifically bind to any activated platelets:

c) separating the intact platelets from the reaction mixture;

d) determining the amount of unbound fibrinogen mimetic in the reaction mixture;

e) comparing the amount of unbound fibrinogen mimetic determined with a known inhibitor of integrin activation;

f) identifying a test compound which has a determined amount of unbound fibrinogen mimetic similar to the known inhibitor of integrin activation; and g) measuring binding of said test compound in intact platelets fixed with paraformaldehyde to determine whether said test compound primarily blocks integrin activation or ligand binding, said test compound being a specific inhibitor of integrin activation in intact platelets if said test compound does not inhibit binding of an integrin binding agent to intact platelets fixed with paraformaldehyde.

2. The method of claim 1 wherein the known integrin activator comprises phorbol myristate acetate, thrombin and adenosine diphosphate.

3. The method of claim 1 wherein the fibrinogen mimetic comprises monoclonal antibody PAC1.

4. The method of claim 1 wherein the fibrinogen mimetic comprises biotinylated PAC1.

* * * * *

UNITED STATES PATENT AND TRADEMARK OFFICE
CERTIFICATE OF CORRECTION

PATENT NO. : 5,561,047

DATED : October 1, 1996

INVENTOR(S) : Shattil

It is certified that error appears in the above-indentified patent and that said Letters Patent is hereby corrected as shown below:

Column 4, line 60, please delete "Am" and insert therefor --An--

Column 5, line 53, please delete "polyethylensorbit" and insert therefor --polyethylensorbitan--

Column 7, line 15, please delete "biotinPAC" and insert therefor --biotin-PAC--

Signed and Sealed this

Fifteenth Day of July, 1997

Attest:

BRUCE LEHMAN

*Attesting Officer*  Commissioner of Patents and Trademarks